United States Patent
Hiraoka et al.

(10) Patent No.: US 6,354,356 B1
(45) Date of Patent: Mar. 12, 2002

(54) METHOD FOR THE DETERMINATION OF THE FORM OF GRAPHITE IN SPHEROIDAL AND COMPACTED/VERMICULAR GRAPHITE CAST IRONS

(75) Inventors: Hidetaka Hiraoka; Mayuki Morinaka, both of Shizuoka; Tsuyoshi Okuzono, Kagoshima, all of (JP)

(73) Assignees: Nissabu Corporation (JP); Yuwa Co., Ltd. (JP)

( * ) Notice: Subject to any disclaimer, the term of this patent is extended or adjusted under 35 U.S.C. 154(b) by 0 days.

(21) Appl. No.: 09/338,190

(22) Filed: Jun. 22, 1999

(30) Foreign Application Priority Data

Jun. 25, 1998 (JP) ............................................. 10-214707

(51) Int. Cl.⁷ ............................................. B22D 46/00
(52) U.S. Cl. ...................... 164/4.1; 164/57.1; 164/58.1; 164/150.1
(58) Field of Search ................................ 164/4.1, 57.1, 164/58.1, 150.1

(56) References Cited

U.S. PATENT DOCUMENTS 5,328,502 A * 7/1994 Bäckerud ...................... 75/377
5,337,799 A * 8/1994 Bäckerud .................... 164/4.1

* cited by examiner

*Primary Examiner*—Nam Nguyen
*Assistant Examiner*—I.-H. Lin
(74) *Attorney, Agent, or Firm*—Bierman, Muserlian and Lucas

(57) ABSTRACT

Disclosed is a method for the determination of the form of graphite in spheroidal and compacted/vermicular cast irons comprising of the first step for collecting molten cast iron, measuring quantity of dissolved oxygen therein and confirming the effect of spherodizing or compacted/vermiculation of graphite in said molten cast iron, the second step for measuring eutectic temperature of said molten cast iron by thermal analyzing, and the third step for comparing said eutectic temperature with a threshold temperature at which said cast iron being separated spherodized graphite phase from compacted/vermiculation phase.

1 Claim, 3 Drawing Sheets

METHOD FOR THE DETERMINATION OF THE FORM OF GRAPHITE IN SPHEROIDAL AND COMPACTED/VERMICULAR GRAPHITE CAST IRONS

BACKGROUND OF THE INVENTION

This invention relates to a method for the determination of the form of graphite in spheroidal and compacted/vermicular (CV) graphite cast irons.

The form of graphite in cast irons is depend on the conditions of solidification. Accordingly, it is preferable to determine the form of graphite before casting.

For most of these cast irons, graphite exists in the form of flake (similar to corn flake), snowflake, spike, C/V and the like. It is, however, sufficient to know one of the forms of graphite, or the portion of spheroidal graphite and C/V graphite mixed in cast irons.

In order to find out the form of graphite in cast irons, usually, there are three methods such as, (1) a method of using an electron microscope, in which a portion of molten cast iron has been collected as a sample, and after solidification of the sample, the surface of the sample is polished and inspected by an electron microscope, (2) a method of measuring velocity of ultrasonic wave passing through the sample, and (3) a method of inspecting eutectic temperature of molten cast irons.

In these methods, the method of using the microscope and ultrasonic waves take much times for investigation and leads to noticeable errors. Accordingly, only the method of the thermal analyzing is practical and useful.

However, in the thermal analyzing method, it is necessary to convert graphite in molten cast iron into spherodized graphite.

In the case of graphite in molten cast iron which has not been converted into spherodized graphite, it is extremely difficult to determine the form of crystallized graphite, even if said molten cast iron is thermally analyzed.

The addition of spheroidizing agent to C/V graphite requires strict control of molten cast irons.

In the light of these problems, it is a principal object of the invention to provide a novel method of the determination of the form of graphite existing in spheroidal graphite cast iron before crystalizing.

It is a further object of the invention to provide a method for the determination of the form of graphite by measuring the quantity of dissolved oxygen containing in molten cast iron and eutectic temperature thereof.

It is a still further object of the invention to a method for estimating the proportion of spheroidal graphite and C/V graphite containing in the molten cast irons by thermal analyzing.

According to the invention, for the purpose of attaining the above objects, in the first step, a portion of the molten cast iron is collected in a sample testing vessel, and then quantity of oxygen dissolved in the molten cast iron by using a conventional oxygen sensor.

From the behavior of oxygen dissolved in molten cast iron, the effectiveness or ineffectiveness of spheroidizing or vermiculating may be decided. When the effect is recognized, eutectic temperature of the molten cast iron can be measured and it is possible to decide the form of graphite in the molten cast iron and the proportion of spheroidal and C/V graphite existing therein.

If the above effect has not been recognized, it is decided that graphite exists in the form of flake.

The quantity of dissolved oxygen depends upon the temperature thereof, and the quantity of dissolved oxygen therein may be measured by using an oxygen sensor is mainly influenced very much by silicon content in the sample.

Accordingly, it is impossible to decide the effect of spheroidizing of the graphite in the molten cast iron from the above quantity of dissolved oxygen may not be decided, and therefore, it is preferable to obtain the relation between the quantity of dissolved oxygen and spheroidizing or compacted/vermiculation.

If, for example, the quantity of dissolved oxygen in the molten cast iron is less than 1 ppm, the effect of spheroidizing or c/v treating will be recognized, but if the quantity of dissolved oxygen is more than 2 ppm, graphite in the molten cast iron will exist in the form of flakes (A or D type), from which it is considered that the effect of C/V treating is not shown.

Even though the chemical composition of flake graphite cast iron (A-type) is identical to one of D-type, there are many differences between the two in ability of forming eutectic graphite nucleus. If a large number of nucleus are existed in eutectic graphite, these nucleus will form flake graphite cast iron (A-type), but if small number of nucleus are existed therein, they will form flake graphite cast iron (D-type), because eutectic austenite in molten cast iron is solidified in the first place.

If eutectic temperature of molten cast iron is higher than about 1141° C. at which spheroidized graphite phase is changed to C/V graphite phase (this temperature is refereed to as "a threshold temperature"), molten cast iron contains a large amount of nucleus to form spheroidal graphite, but if it is lower than the threshold temperature, it contains a small amount of nucleus.

Accordingly, the eutectic temperature of molten cast iron in each of the above samples may be measured by using a cup like sampling vessel. Then it is able to decide that if the eutectic temperature of the sample is higher than the threshold temperature, it forms spherodized graphite cast iron, but if it is lower than the threshold temperature, it forms C/V graphite cast iron.

BRIEF DESCRIPTION OF THE DRAWINGS

The method will be described with reference to the drawings in which.

DETAILED DESCRIPTION OF THE INVENTION

In order to confirm the threshold temperature of graphite cast irons, the following experiences were carried out by the inventors. 1% (by weight) of spheroidizing agent, Fe-45%Si-3%Mg, was added to molten pig iron, Fe-35%C-1.4%Si, and kept it at a constant temperature. Then the samples No. 1 –No. 4 were collected every five (5) minutes. Optical photomicrographs of these samples No. 1 to No. 4 are respectively shown in FIGS. 1 to 4.

Figure 1:
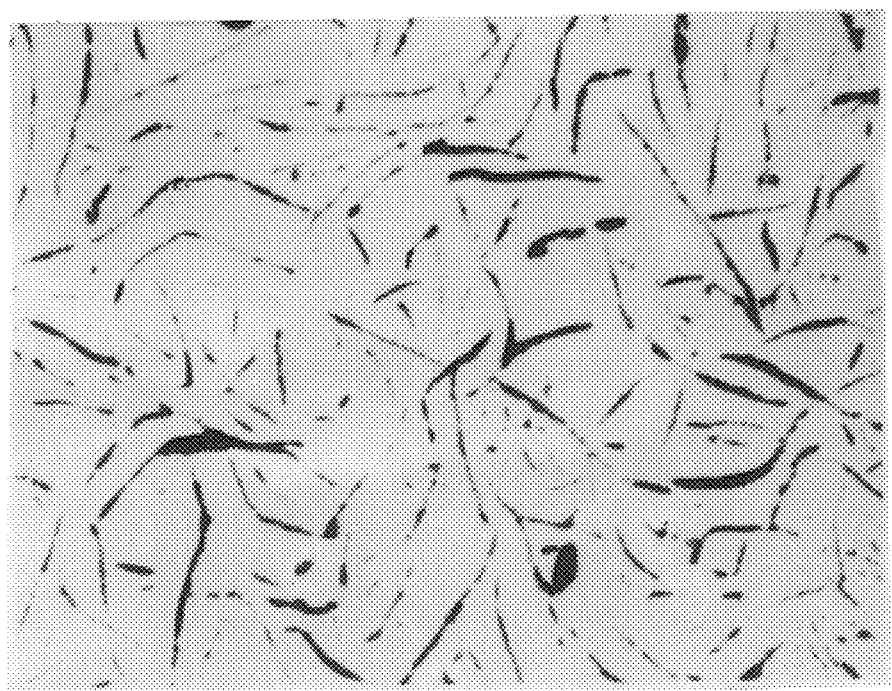
FIG. 1 is a photomicrograph showing the type of graphite in Sample No. 1.
Figure 2:
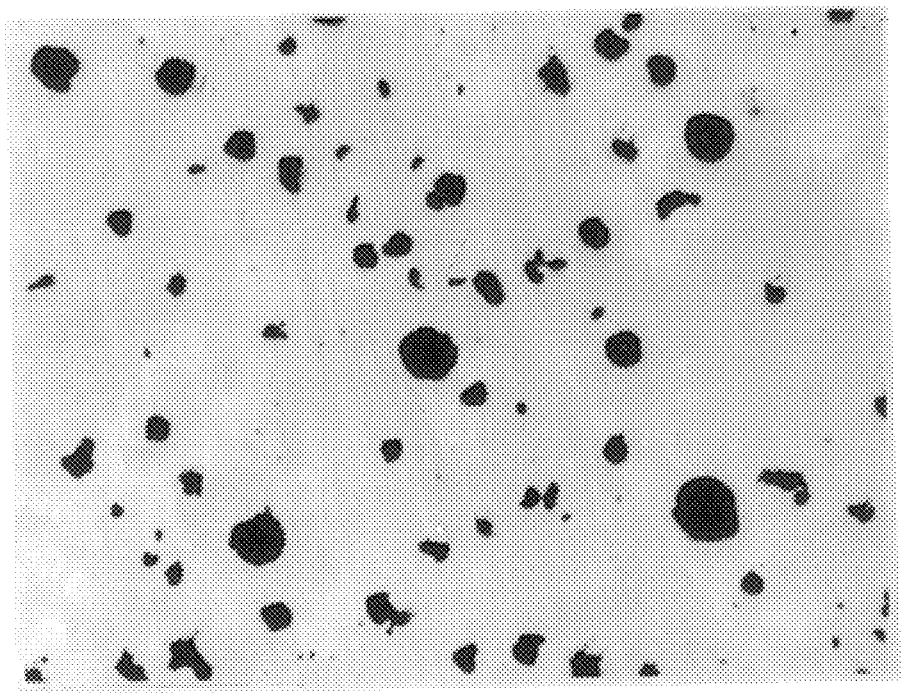
FIG. 2 is a photomicrograph showing the type of graphite in Sample No. 2.
Figure 3:
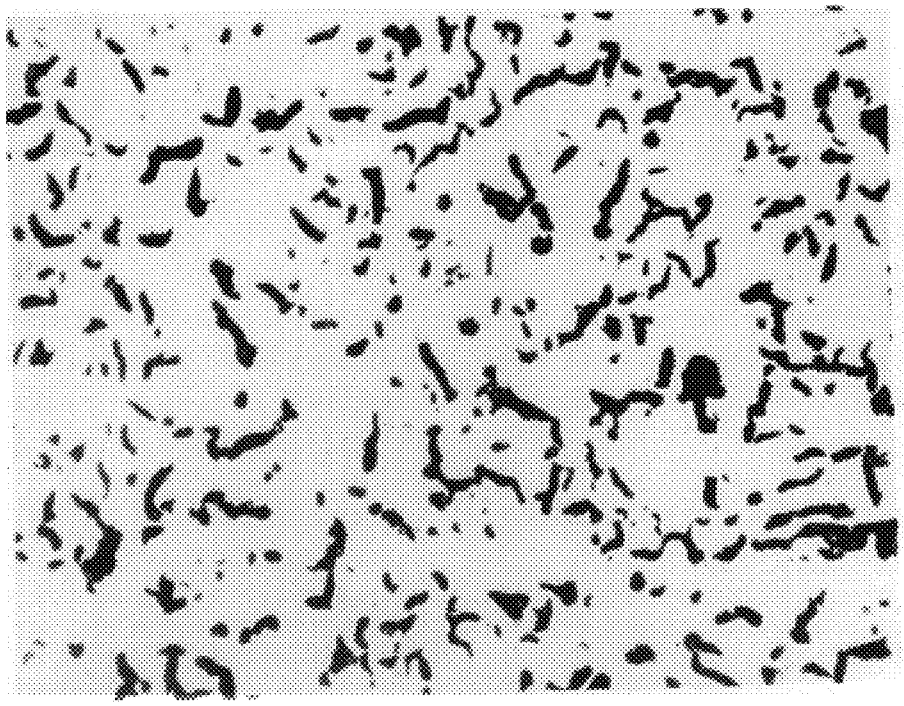
FIG. 3 is a photomicrograph showing the type of graphite in Sample No. 3.
Figure 4:
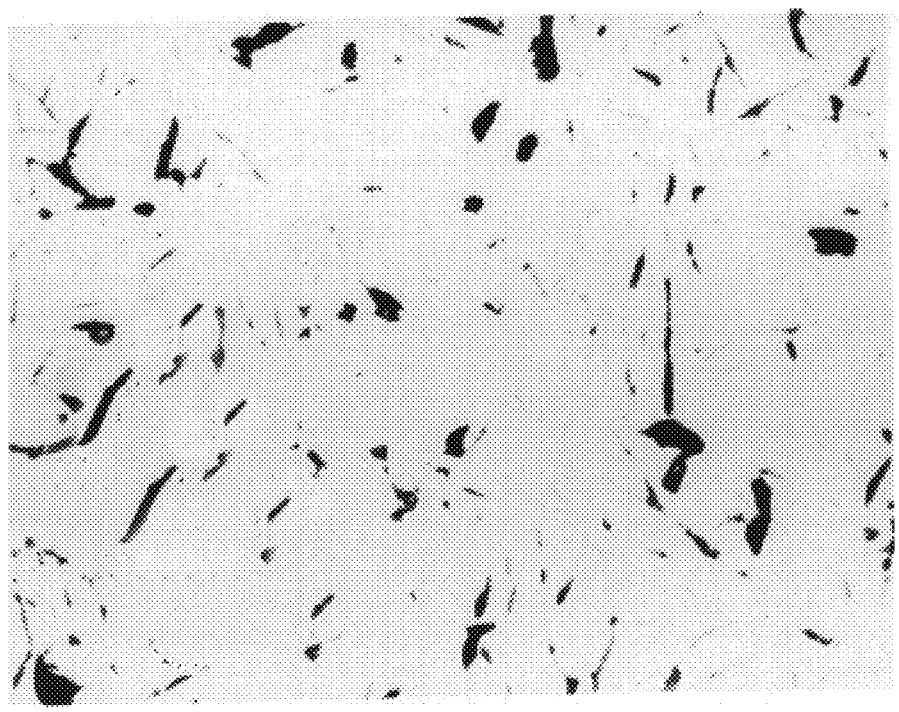
FIG. 4 is a photomicrograph showing the type of graphite in Sample No. 4.
Figure 5:
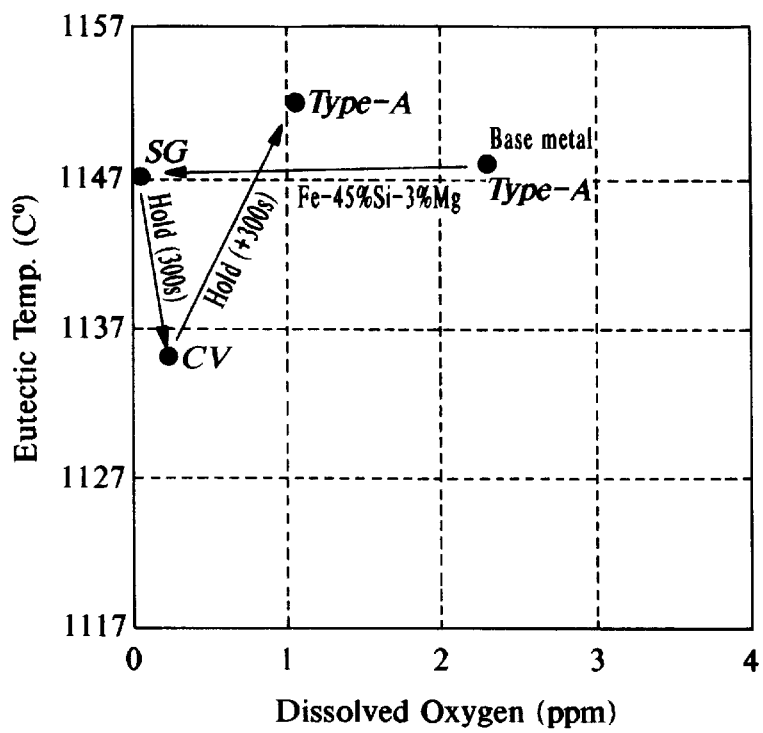
FIG. 5 is a diagram illustrating a relation between quantity of dissolved oxygen and eutectic temperature of the sample No. 4.
Figure 6:
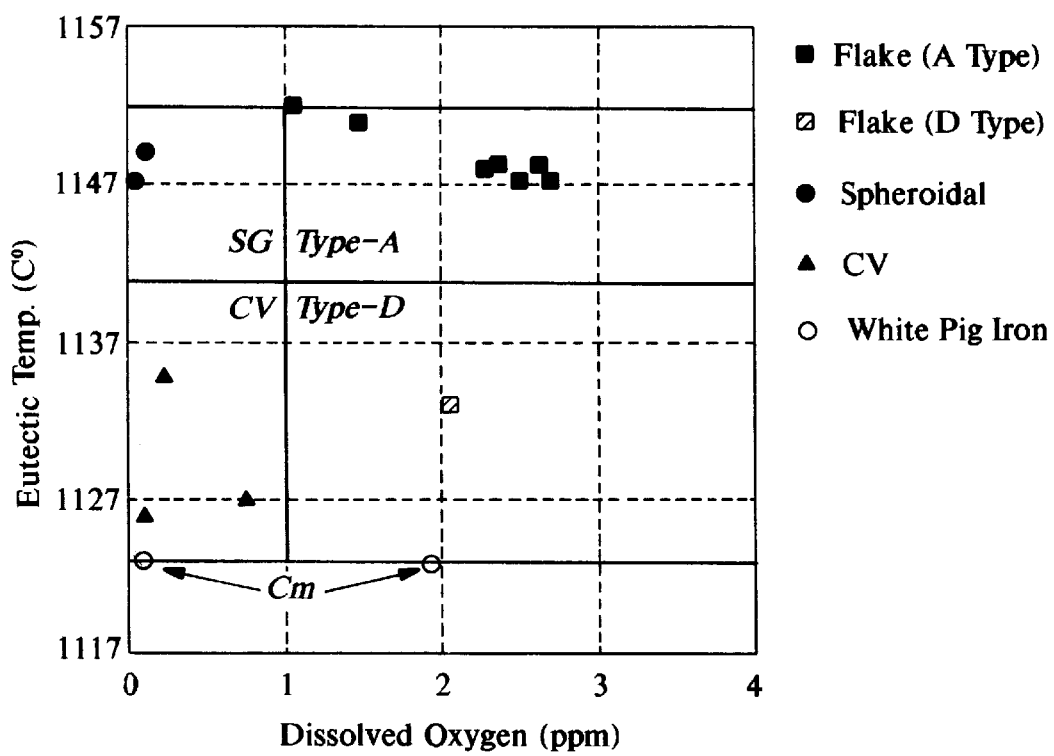
FIG. 6 is a diagram illustrating a relation between quantity of dissolved oxygen and eutectic temperature obtained in the second experiment.

As shown in FIG. 4 which illustrates the relation between the quantity of dissolved oxygen and eutectic temperature of the sample No. 4.

(Experiment 1)

In the first step, Fe-3.2%C-1.7%Si cast iron is melted in a graphite crucible by using a high frequency electric induction furnace. After 30 minutes, the cast iron was completely melted, and after 40 minutes, the temperature of the melting cast iron is reached at 1500° C. and 2.7 ppm of dissolved oxide is measured by an oxygen sensor.

From the above, it is considered that the molten cast iron is converted into spherodized or C/V graphite cast iron, or white pig iron.

In the second step, 0.2% of mischmetal is added to molten cast iron, and 0.7 ppm of dissolved oxygen was measured therefrom. Accordingly, it is decided that the cast iron will form spheriodized or C/V graphite cast iron or white pig iron. Mischmetal is added to the molten cast iron for the reason that if a large quantity of molten oxide is contained, it is impossible to recognize the effect of spherodization or compact verniculation.

In the third step, two sampling vessels were used for measuring the eutectic temperature of molten cast iron.

No additive had been used to the first sampling vessel, but 0.2% mischelmetal had been added into the second vessel. Molten cast iron was poured into both sampling vessels at the same time.

It is found that eutectic temperatures of molten cast iron in the first and second vessels is identical to 1118° C., and therefore, the molten metal in both vessels is recognized as white pig iron.

If eutectic temperature of molten cast iron is higher than that of white pig iron and lower than 1141° C., graphite exists in the form of C/V, but if eutectic temperature is higher than 1141° C., graphite exists in the form of spheroidal. Accordingly, it may be defined that 1141° C. is the threshold temperature between the two, and chemical compositions of each phase will be shown in the following table.

TABLE

| | Quantity of Dissolved Oxygen | |
|---|---|---|
| Eutectic Temperature | Higher than 2 ppm | Lower than 1 ppm |
| Higher than 1141° C. | Flake (A type) | Spheroidized graphite |
| Lower than 1141° C. | Flake (D type) White Pig Iron | C/V graphite White Pig Iron |
| Same as Eutectic Temp. of White Pig Iron | White Pig Iron | White Pig Iron |

From the above results, it may be decided that graphite exists in the form of C/V in molten cast iron contained in the second sampling vessel used in experiment 1. Thus, the molten cast iron may be solidified as C/V graphite cast iron.

(Experiment 2)

Main raw material consisting of cast iron, steel scraps and Fe-75%Si is melted in a high frequency electric induction furnace to form Fe-3.7%C-2.3Si alloy. The material is completely melted in 30 minutes and temperature of molten metal is reached to 1500° C. in 40 minutes. At that time it is found that 2.9 pm oxygen is dissolved in molten metal.

When the above molten metal has been solidified, graphite exists in the form of flake therein. Accordingly, in order to convert it into spheroidal graphite, convenient 1% C/V additive is added into the above molten metal in the second step. By using an oxygen sensor, it is found that 0.5 pm dissolved oxygen is contained therein.

It is recognized that when the molten metal has directly been solidified, graphite exists in the form of spheroidal.

In the third step, as the same manner in the first experiment, any additive has not been added to the first sampling vessel, and 0.2% mischmetal is added to the second sampling vessel in order to fix oxygen in molten cast iron poured therein.

It is found that eutectic temperature of molten metal in each of the first and second vessels is 1146° C. and 1110° C.

For the reason that eutectic temperature of molten cast iron in the first vessel is higher than the threshold temperature of 1141° C., it is recognized that a large amount of graphite exists in the form of spherodized therein.

Accordingly, it is possible to decide that a large amount of spherodized graphite is contained in molten cast iron.

What is claimed is:

1. A method for the determination of the form of graphite in spheroidal and compacted/vermicular cast iron comprising the steps of:

(a) sampling molten cast iron in a sampling vessel and measuring the quantity of oxygen dissolved in the sample of said molten cast iron by using an oxygen sensor, (b) distinguishing the presence or absence of effect of spheroidal or compact/vermicular treatment with respect to the sample of said molten cast iron, (c) measuring eutectic temperature of the sample of said molten cast iron which has the effect of spheroidal or compacted/vermiculation treatment, and (d) comparing the measured eutectic temperature with threshold temperature (1141° C.) of the spheroidal cast iron and the compacted/vermiculation cast iron.

* * * * *